US010274477B2

(12) United States Patent
Rosenstein et al.

(10) Patent No.: US 10,274,477 B2
(45) Date of Patent: Apr. 30, 2019

(54) HIGH-SPEED MOLECULAR DIAGNOSTICS

(71) Applicant: Brown University, Providence, RI (US)

(72) Inventors: Jacob Karl Rosenstein, Providence, RI (US); Shanshan Dai, Providence, RI (US)

(73) Assignee: Brown University, Providence, RI (US)

( * ) Notice: Subject to any disclaimer, the term of this patent is extended or adjusted under 35 U.S.C. 154(b) by 686 days.

(21) Appl. No.: 14/967,215

(22) Filed: Dec. 11, 2015

(65) Prior Publication Data

US 2016/0169865 A1    Jun. 16, 2016

Related U.S. Application Data

(60) Provisional application No. 62/092,200, filed on Dec. 15, 2014.

(51) Int. Cl.
| | | |
|---|---|---|
| G01R 22/00 | (2006.01) | |
| G01N 33/487 | (2006.01) | |
| C12Q 1/6874 | (2018.01) | |

(52) U.S. Cl.
CPC ..... *G01N 33/48721* (2013.01); *C12Q 1/6874* (2013.01)

(58) Field of Classification Search
CPC .......... G01N 33/48721; C12Q 1/6874
See application file for complete search history.

(56) References Cited

U.S. PATENT DOCUMENTS

| | | |
|---|---|---|
| 5,103,230 A | 4/1992 | Kalthoff et al. |
| 2002/0140439 A1 | 10/2002 | Enam et al. |
| 2002/0149413 A1 | 10/2002 | Denison |
| 2012/0043972 A1 | 2/2012 | Jayaraman |
| 2012/0250203 A1* | 10/2012 | Makihara ............. G01R 31/362 361/86 |

OTHER PUBLICATIONS

PCT International Search Report and Written Opinion for PCT/US2015/065401, dated May 6, 2016; 11 pages.
Shanshan Dai et al, "A Dual-Mode Low-Noise Nanosensor Front-End with 155-dB Dynamic Range," IEEE Biomedical Circuits and Systems Conference (BIOCAS), Oct. 2015; 4 pages.

\* cited by examiner

*Primary Examiner* — Clayton E. LaBalle
*Assistant Examiner* — Jas A Sanghera
(74) *Attorney, Agent, or Firm* — Adler Pollock & Sheehan P.C.; Daniel J. Holmander, Esq.

(57) ABSTRACT

A system for high-speed molecular diagnostics includes a self-resetting continuous-time integrator configured to integrate an input current on one of a plurality of integration capacitors to generate an integrated voltage. A self-resetting continuous-time differentiator is configured to differentiate the integrated voltage on one of a plurality of differentiating capacitors to generate an output voltage proportional to the input current. A fixed-threshold window comparator is configured to reset one of the plurality of integration capacitors, reset one of the plurality of differentiating capacitors, open a second one of the plurality of integration capacitors and open a second one of the plurality of differentiating capacitors in response to the integrated voltage exceeding a voltage range.

20 Claims, 8 Drawing Sheets

HIGH-SPEED MOLECULAR DIAGNOSTICS

CROSS-REFERENCE TO RELATED APPLICATIONS

This application is a utility application claiming priority to U.S. Provisional Application Ser. No. 62/092,200 filed on Dec. 15, 2014 entitled "HIGH-SPEED TUNNELING-RECOGNITION DIAGNOSTICS," the entirety of which is incorporated by reference herein.

FIELD

This disclosure relates generally to molecular diagnostics, and more specifically to low noise and high dynamic range bioelectronics for high-speed molecular diagnostics.

BACKGROUND

Molecular diagnostics includes the analysis of single biomolecules, which are faster, weaker, and more stochastic than their macroscale counterparts. Consequently, single-molecule measurements are regularly constrained by poor signal-to-noise ratios, and temporal resolution is commonly sacrificed in exchange for lower noise amplitudes. Optical and mechanical nanosensors may operate near their intrinsic noise floors, but electronic platforms often plateau at limits jointly determined by the sensors together with their electronic acquisition circuits.

Acquisition circuitry based on high-value pseudo-resistors, timed integrators with an external frequency reference, switched-capacitor networks and logarithmic feedback elements face difficult tradeoffs between bandwidth, noise, and dynamic range. Although resistive transimpedance amplifiers have a straightforward implementation, they have relatively low performance. Discrete-time systems have higher performance but lower bandwidth. Logarithmic systems offer wide dynamic range but are limited by poor linearity and temperature dependence.

BRIEF SUMMARY

As will be appreciated, embodiments as disclosed herein include at least the following. In one embodiment, a method for high-speed molecular diagnostics comprises integrating charge stored thereby on a first resettable capacitor of an integrator. A first one and a second one of a plurality of clock phases is switched in response to the integrated voltage exceeding a voltage range. The first resettable capacitor is shorted with a first switch controlled by the first one of the plurality of clock phases to equalize the first integrated charge stored on the first resettable capacitor. A second resettable capacitor is opened with a second switch controlled by a second one of the plurality of clock phases, wherein the second resettable capacitor is connected in series with the first resettable capacitor in a negative feedback loop of the integrator.

Alternative embodiments of the method for high-speed molecular diagnostics include one of the following features, or any combination thereof. The integrated voltage is differentiated to generate an output voltage proportional to the input current. A third resettable capacitor is shorted with a third switch controlled by the first one of the plurality of clock phases to equalize a differentiated charge stored on the third resettable capacitor by an differentiator. A fourth resettable capacitor is opened with a fourth switch controlled by the second one of the plurality of clock phases, wherein the fourth resettable capacitor is connected in series with the third resettable capacitor forming an input to the differentiator. A third resettable capacitor is shorted with a third switch controlled by the second one of the plurality of clock phases to equalize a differentiated charge stored on the third resettable capacitor by an differentiator. A fourth resettable capacitor is opened with a fourth switch controlled by the first one of the plurality of clock phases, wherein the fourth resettable capacitor is connected in series with the third resettable capacitor forming an input to the differentiator. An output frequency having a frequency proportional to the input current is generated, by toggling a bistable device in response to the integrated voltage exceeding the voltage range. The integrated voltage exceeding the voltage range comprises one of the integrated voltage being greater than an upper threshold voltage and the integrated voltage being less than a lower threshold voltage. The input current on the second resettable capacitor is integrated to generate the integrated voltage proportional to a second integrated charge stored thereby, in response to opening the second resettable capacitor with the second switch. The first integrated charge is equal to the second integrated charge.

In another embodiment, a device for high-speed molecular diagnostics comprises an integrator configured to generate an integrated voltage by integrating an input current received thereto, the integrator comprising a first resettable capacitor connected in series with a second resettable capacitor in a negative feedback loop of an amplifier. A first comparator is configured to switch a state of a first multiphase device in response to the integrated voltage of the integrator exceeding a first threshold voltage of the first comparator, wherein the first multiphase device provides a plurality of non-overlapping clock phases. A first switch is connected in parallel with the first resettable capacitor, the first switch controlled by a first one of the plurality of non-overlapping clock phases. A second switch is connected in parallel with the second resettable capacitor, the second switch controlled by a second one of the plurality of non-overlapping clock phases.

Alternative embodiments of the device for high-speed molecular diagnostics include one of the following features, or any combination thereof. A differentiator is configured to generate an output voltage proportional to the input current comprising a third resettable capacitor and a fourth resettable capacitor connected in series between the integrated voltage and an inverting input of an amplifier, the third resettable capacitor is configured to be shorted when the fourth resettable capacitor is open, and the fourth resettable capacitor is configured to be shorted when the third resettable capacitor is open. A bistable device is configured to generate an output frequency having a frequency proportional to the input current in response to the integrated voltage exceeding the voltage range. A second comparator has a second threshold voltage, the state of the first multiphase device switches in response to the voltage output of the integrator exceeding one of the first threshold voltage and the second threshold voltage. At least one of the first threshold voltage and the second threshold voltage includes a hysteresis value. The first resettable capacitor has a first capacitance equal to a second capacitance of the second resettable capacitor. At least one of the first switch and the second switch comprises a complementary pair of field effect transistors.

In another embodiment, a system for high-speed molecular diagnostics comprises a self-resetting continuous-time integrator configured to integrate an input current on one of a plurality of integration capacitors to generate an integrated voltage. A self-resetting continuous-time differentiator is configured to differentiate the integrated voltage on one of a plurality of differentiating capacitors to generate an output voltage proportional to the input current. A fixed-threshold window comparator is configured to reset the one of the plurality of integration capacitors, reset the one of the plurality of differentiating capacitors, open a second one of the plurality of integration capacitors and open a second one of the plurality of differentiating capacitors in response to the integrated voltage exceeding a voltage range.

Alternative embodiments of the system for high-speed molecular diagnostics include one of the following features, or any combination thereof. A bistable device is configured to generate an output frequency proportional to the input current by toggling in response to the integrated voltage exceeding the voltage range. The input current is an ionic current conducting through a nanopore. The input current is an electron tunneling current conducting through a molecule in a tunneling gap. The input current is used for one of DNA sequencing and biomolecule detection.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Embodiments of molecular diagnostic methods and systems described herein provide for faster, cheaper and higher fidelity diagnostics applicable to numerous fields, including but not limited to DNA sequencing, and single-molecule protein detection. Self-resetting continuous-time measurement of ion channels, nanopores, tunneling junctions and other nanosensors enable the determination of sub-microsecond real-time trajectories of single molecules, thereby bridging the temporal gap between experimental data and molecular dynamics simulations. High-resolution experimental measurements of molecular conductance at faster timescales allow the recognition of complex energy landscapes and non-ergodic molecular processes. Furthermore, the following embodiments provide for large parallel sensing arrays allowing rapid and cost effective DNA sequencing.

By using a plurality of matched self-resetting capacitors with local charge balancing in an integrator-differentiator, undesirable transient reset glitches in the output of the integrator-differentiator are eliminated. These glitches could otherwise saturate the differentiator and produce long recovery times during which time the sensed input current would not be observable. Furthermore, the use of local charge balancing prevents the integrator from entering into unity-gain feedback, thus further guarding against saturation of the differentiator.

Figure 1:
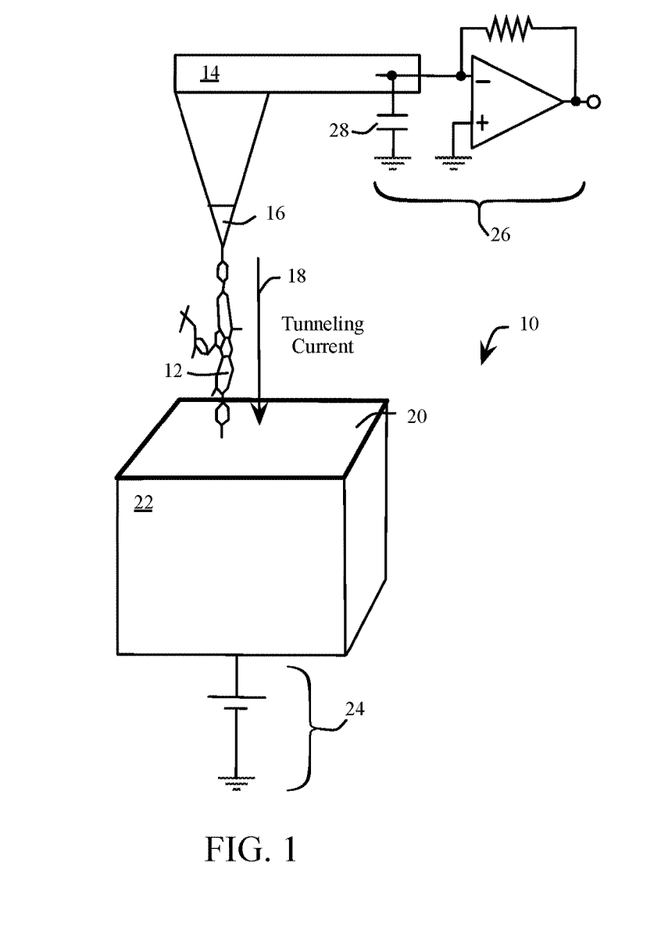
FIG. 1 is a schematic view of a Scanning Tunneling Microscope (STM) with current measured through a probe.

FIG. 1, FIG. 2, FIG. 3 and FIG. 4 show representative embodiments of systems used for molecular diagnostics, each of which require high bandwidth, high resolution measurements in a noisy environment. FIG. 1 shows an embodiment 10 of an STM used to analyze a protein molecule 12. A cantilever 14 includes an atomically sharp metallic tip 16 for passing a tunneling current 18 through the molecule 12 to a metallic surface 20 of a semiconductor substrate 22. The substrate 22 is capacitively coupled to ground with a capacitor 24. A discrete amplifier 26 with a parasitic capacitance 28, measures the electron tunneling current 18.

Figure 2:
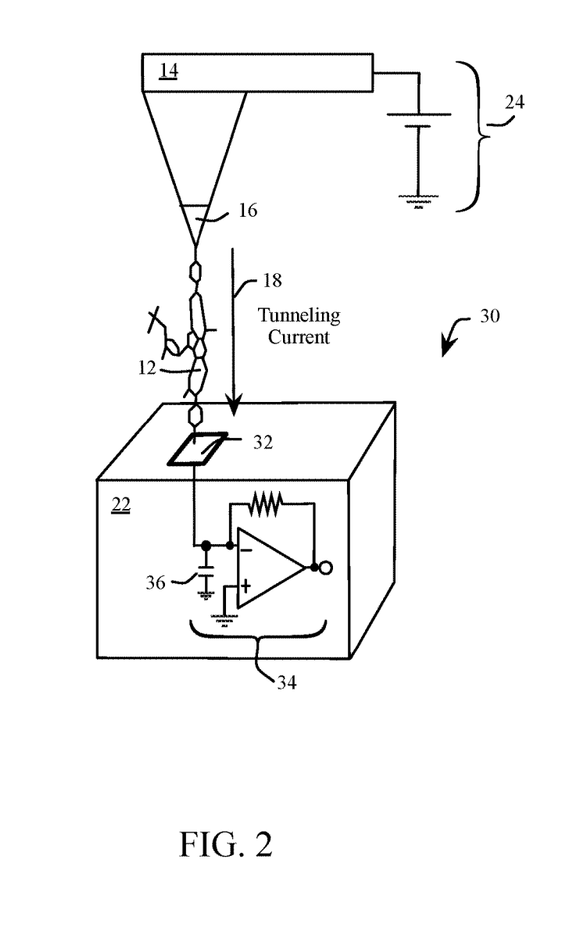
FIG. 2 is a schematic view of a high-speed inverted tunneling platform using the surface of an active CMOS preamplifier.

FIG. 2 shows an improved embodiment 30 of an STM, with reduced parasitics and higher bandwidth over the embodiment 10 of FIG. 1. The tunneling current 18 is measured through a smaller metallic surface 32 on the semiconductor substrate 22. The amplifier 34 is integrated into the substrate 22, and consequently has a significantly reduced input capacitance 36, contributing to higher bandwidth measurements.

Figure 3:
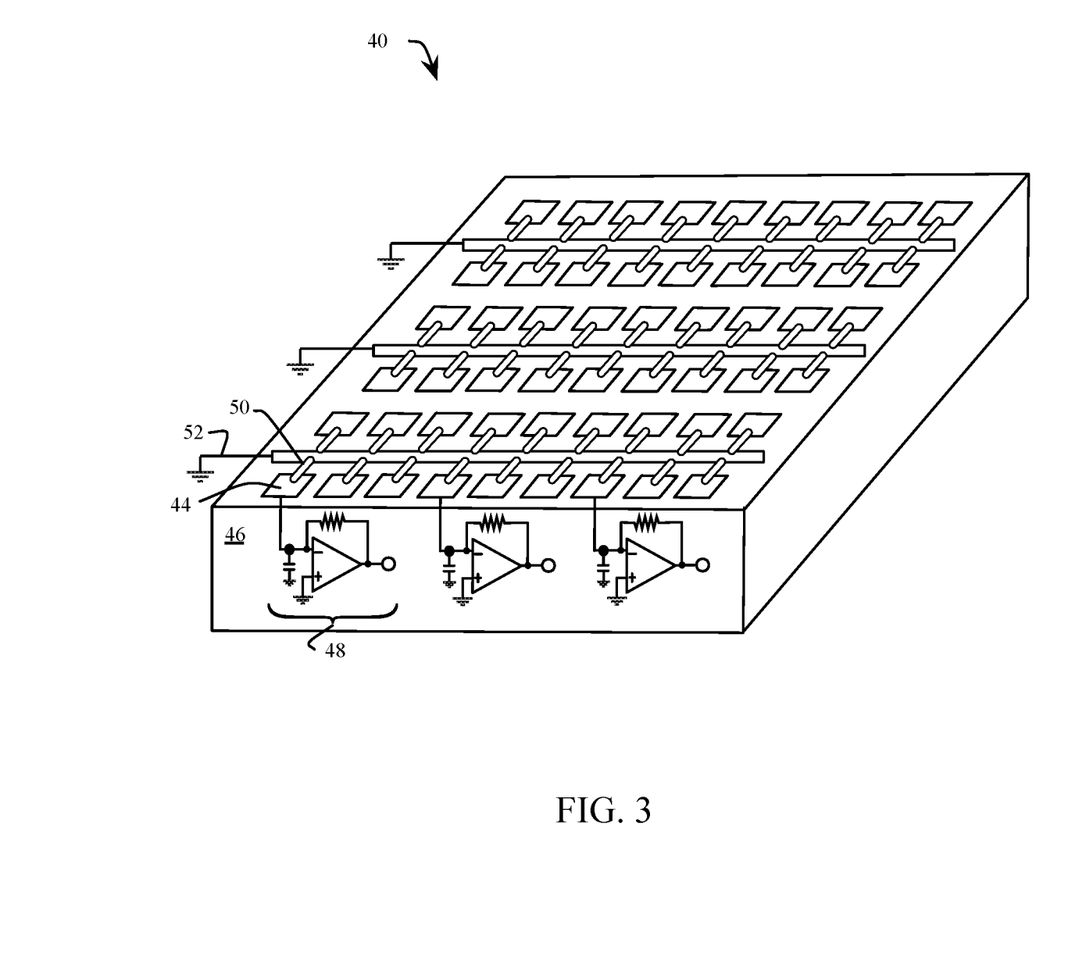
FIG. 3 is a perspective view of a monolithic integrated system with combined preamplifiers and sensor arrays, using nanogap tunneling detectors.

The embodiment 40 of FIG. 3 includes a large-scale array for rapid molecular diagnostics using nanogap tunneling detectors rather than a scanning STM probe. Each metallic surface 44 is connected to a corresponding nanogap tunneling detector 50, which is biased (e.g. to ground) 52. Each metallic surface 44 also connects to a corresponding amplifier 48 to detect and amplify the tunneling current.

Arrays of single-molecule sensors as shown in FIG. 3 are desirable for increased throughput in molecular assays and spatially-resolved chemical imaging. In various embodiments the high frame data rates are managed by data compression to increase achievable frame rates and decrease storage requirements. Although there is little spatial correlation between single-molecule detectors, compression takes advantage of the temporal properties of each independent trace. Embodiments of data compression systems and methods for biomolecule diagnostics take advantage of the fact that (i) not all channel operate simultaneously, and sample rates are adjust accordingly, (ii) single-molecule data is often inherently amplitude-quantized, (iii) single-molecule traces can have predictable shapes, albeit at stochastic intervals, and (iv) the underlying statistics of fluctuating data can change slower than the raw signals. Various embodiments use hardware compression strategies with wavelet kernel compression, non-uniform sampling, and event-based signal acquisition.

Figure 4:
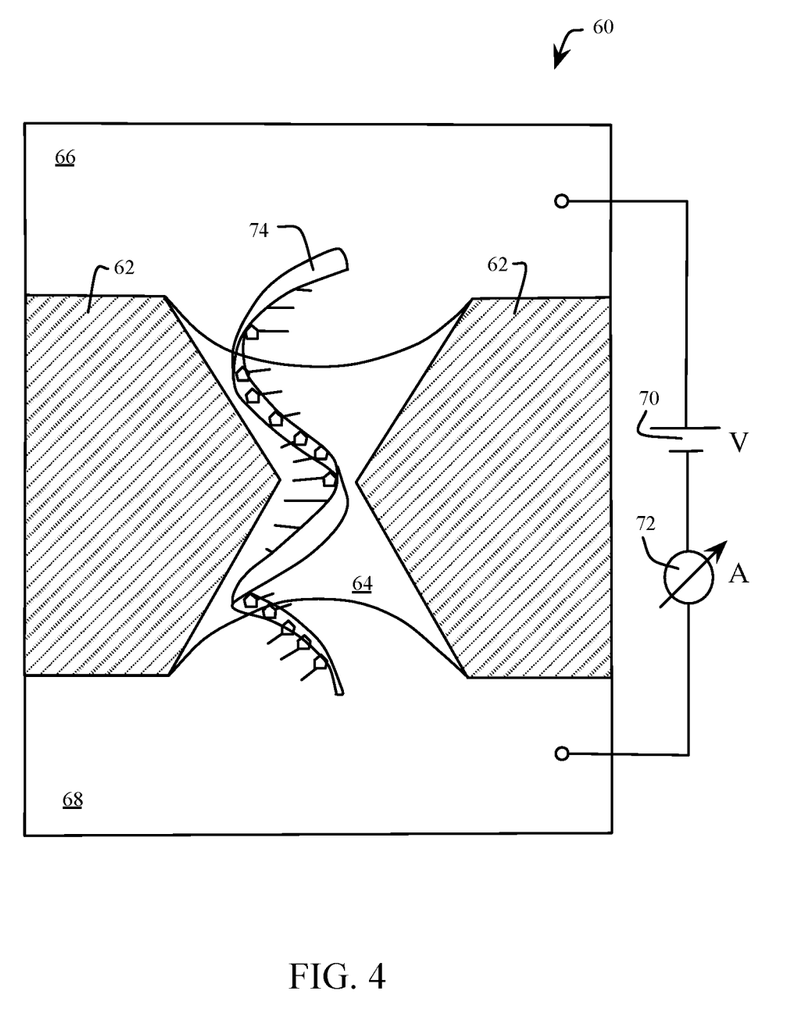
FIG. 4 is a cross-section view of a nanopore for DeoxyriboNucleic Acid (DNA) sequencing.

FIG. 4 shows an embodiment 60 of a system for molecular diagnostics based on fluctuations of ionic conduction through a nanopore. An insulating membrane 62 includes a nanopore 64. An aqueous solution of ions 66 and 68 pass through the nanopore 64 under a bias 70. Changes in ionic current are measured by a current measuring device 72, based on small changes to the geometry or electrostatics of the nanopore, for example by the passage of a DNA sample 74. The changes in current corresponding to the passage of the DNA sample 74 through the nanopore 64 are small and occur in a finite timescale. In one example, a DNA sample 74 transported through the nanopore 64 produces 0.16 picoamperes at a rate of over one million bases per second. Measuring the nanosensor current levels produced by the STM probe of FIG. 2 and FIG. 3, the nanopore sensor of FIG. 4 or other molecular diagnostic systems requires acquisition circuitry that can detect low currents, in a low signal to noise (SNR) environment with high bandwidth and high resolution.

Figure 5:
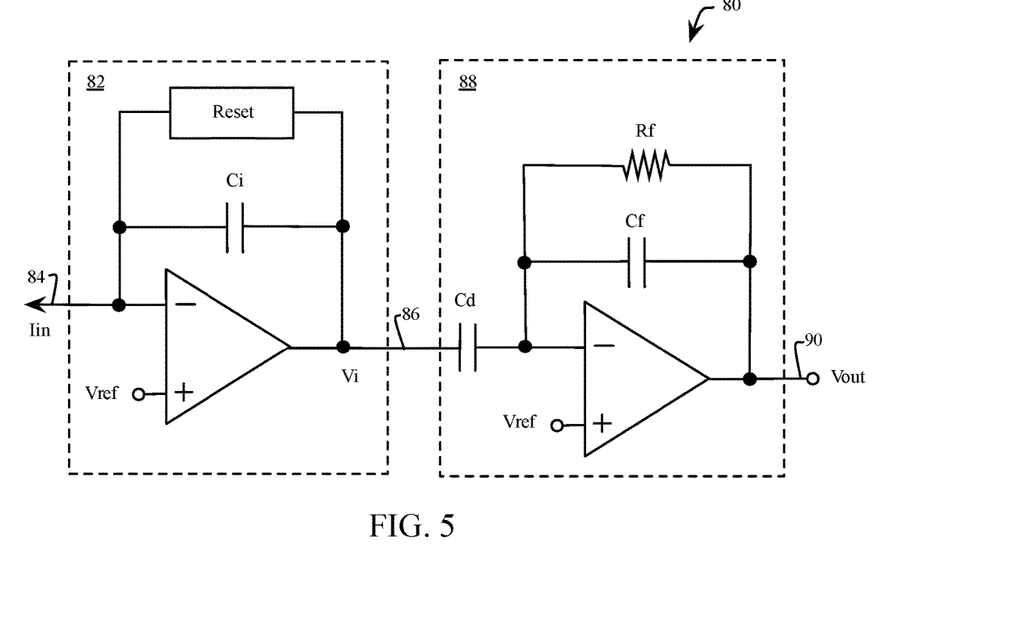
FIG. 5 is a schematic view of an integrator-differentiator.

FIG. 5 shows an embodiment 80 of an integrator-differentiator core suitable for measuring low currents levels. An integrator 82 integrates an input current 84 from a sensor and produces an integrated output 86. A differentiator 88 measures the integrated voltage output 86 to produce a measured output voltage 90 proportional to the input current 84. Various noise sources limit the stability and bandwidth of this embodiment 80. Specifically, parasitic capacitances are detrimental to the feedback stability and input-referred noise of the circuit, thus requiring a reduction in bandwidth to maintain loop stability. While the input referred noise of the embodiment 80 is very low compared to a resistive transimpedance amplifier, the integrator is prone to saturation, thus requiring a discrete reset, which puts the integrator into unity gain feedback, or alternatively the use of DC offset compensation, which introduces broadband noise.

Figure 6:
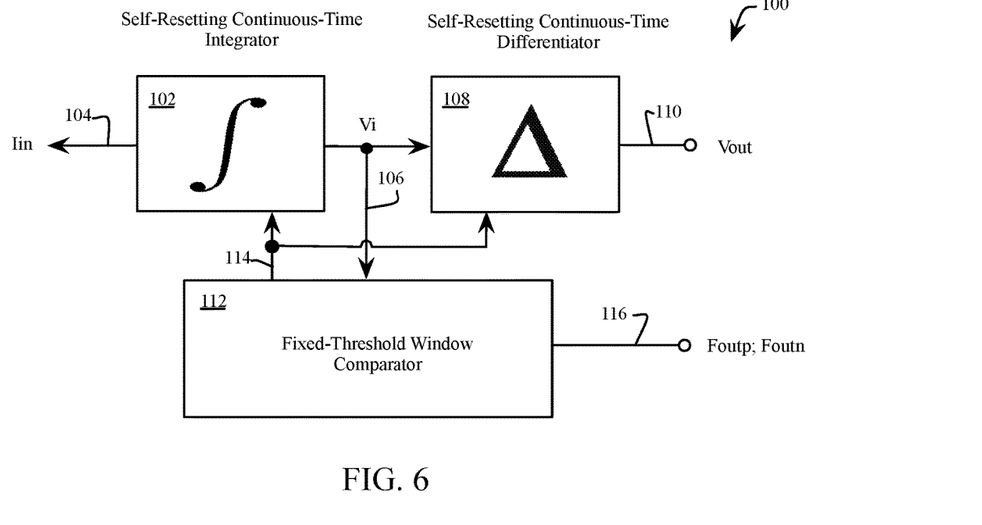
FIG. 6 is a functional block diagram of a self-resetting continuous-time integrator-differentiator for high-speed diagnostics.

FIG. 6 shows an embodiment 100 with an improved architecture over the embodiment 80, with lower noise and thus higher bandwidth operation. A self-resetting continuous-time integrator 102 measures the input current 104 to produce an integrated voltage output 106. The integrated voltage output 106 is differentiated by a self-resetting continuous-time differentiator 108 to produce a measured output voltage 110, which is proportional to the input current 104. The integrated voltage output 106 is compared to a threshold with a fixed-threshold window comparator 112 to generate reset signals 114 for resetting the self-resetting continuous-time integrator 102 and the self-resetting continuous-time differentiator. The fixed-threshold window comparator 112 also generates one or more measured frequency outputs 116, which are proportional to the input current 104.

The embodiment 100 thus provides concurrent voltage and frequency outputs, each being proportional to the input current 104. In one example, the measured output voltage and the measured frequency output are compared for equivalency to detect saturation of the self-resetting continuous-time differentiator 108. In another example, the fixed-threshold window comparator 112 includes an upper and a lower threshold for measurement of bipolar currents. In another example, one or more thresholds of the fixed-threshold window comparator 112 limit a voltage range of the integrated voltage output 106 to prevent saturation of the self-resetting continuous-time differentiator 108. The self-resetting architecture of embodiment 100 is self-balancing and thus maintains a low level of input referred noise, and high bandwidth.

Figure 7:
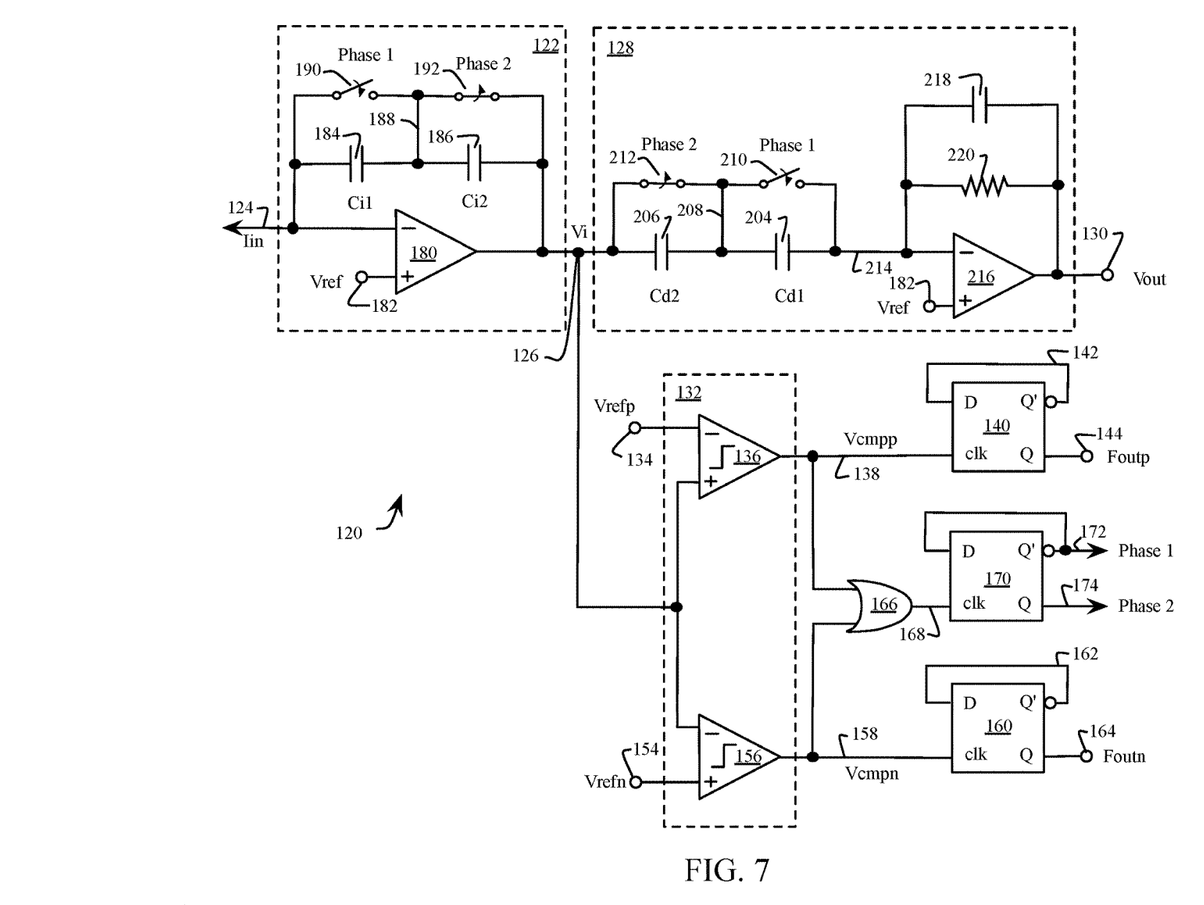
FIG. 7 is a schematic view of an embodiment of a self-resetting continuous-time integrator-differentiator for high-speed diagnostics.

Referring to FIG. 7, an embodiment 120 of the self-resetting continuous-time architecture of FIG. 6 includes an integrator 122 for integrating an input current 124 to produce an integrated voltage 126. The integrated voltage 126 is differentiated by a differentiator 128 to produce a measured output voltage 130.

The integrated voltage 126 is compared with a fixed-threshold window comparator 132 to determine if the integrated voltage has exceeded a range. Specifically, the integrated voltage 126 is compared to a positive reference voltage 134 with a positive threshold comparator 136 to provide a positive compared voltage 138. In various embodiments, the positive threshold comparator 136 is a comparator with hysteresis (e.g. a Schmitt trigger). The positive transition of the positive compared voltage 138 toggles a bistable device 140 (e.g. a D-flop configured with a feedback connection 142 between an inverted output and the data input) to generate a positive frequency output 144. In various embodiments, the integrated voltage 126 is also compared to a negative reference voltage 154 with a negative threshold comparator 156 to provide a negative compared voltage 158. In various embodiments, the negative threshold comparator 156 is a comparator with hysteresis (e.g. a Schmitt trigger). The positive transition of the negative compared voltage 158 toggles a bistable device 160 (e.g. a D-flop configured with a feedback connection 162 between an inverted output and the data input) to generate a negative frequency output 164.

Various embodiments include comparing the integrated voltage 126 to the positive reference voltage 134, the negative reference voltage 154 or both the positive reference voltage 134 and the negative reference voltage 154. It should be understood that the polarity of the respective outputs of the threshold comparators 136 and 156 can be inverted, either with an inversion stage or by swapping the order of their respective inputs, with a corresponding inversion to the clock inputs of the respective bistable devices 140 and 160, and other devices connected thereto. In other embodiments, the bistable devices 140 and 160 are J-K Flip-Flops.

In some embodiments, the positive comparator voltage 138 and the negative comparator voltage 158 are compared with a logical "OR" gate 166 to generate a transition voltage 168. For embodiments that only include one of the positive comparator voltage 138 and the negative comparator voltage 158, the respective comparator voltage is equivalent to the transition voltage 168. The transition voltage 168 toggles a multi-phase device 170 to toggle a state of a first clock phase 172 and a second clock phase 174, whereby the two clock phases 172 and 174 are non-overlapping. In some embodiments, the multi-phase device 170 is a modified D-flop configured with a feedback connection 172 between an inverted output and the data input, and configured to generate non-overlapping clock phases.

The integrator 122 includes a differential amplifier 180, which amplifies a difference between the input current 124 and a reference 182 to produce the integrated voltage 126. The differential amplifier 180 further includes, between the integrated voltage 126 output and the input current 124 input, a first integrator capacitor 184 connected in series, at a node 188, with a second integrator capacitor 186. The first integrator capacitor 184 is connected in parallel with a switch 190 controlled by the first clock phase 172. The second integrator capacitor 186 is connected in parallel with a switch 192 controlled by the second clock phase 174. The integrator 122 alternately integrates charge on either the first integrator capacitor 184, while the second integrator capacitor 186 is shorted by the switch 192, or on the second integrator capacitor 186, while the first integrator capacitor 184 is shorted by the switch 190.

In various embodiments, the switches 190 and 192 are formed by complementary pairs of field effect transistors (FETs) configured, through appropriate transistor dimensioning, to minimize charge injection from the clock phase to the respective integrator capacitor when the respective integrator capacitor is being reset (e.g. shorted by the switch). In various embodiments, the first integrator capacitor 184 has a same capacitance as the second integrator capacitor 186, within reasonable manufacturing tolerances.

The differentiator 128 includes a second differentiator capacitor 204 in series, at a node 208, with a first differentiator capacitor 206. The first differentiator capacitor 204 is connected in parallel with a switch 210 controlled by the first clock phase 172. The second differentiator capacitor 206 is connected in parallel with a switch 212 controlled by the second clock phase 174. The differentiator 128 alternately integrates charge on either the first differentiator capacitor 204, while the second differentiator capacitor 206 is shorted by the switch 212, or on the second differentiator capacitor 206, while the first differentiator capacitor 204 is shorted by the switch 210. The first differentiator capacitor 204 in series with the second differentiator capacitor 206 couples the integrated voltage 126 to a node 214. The differentiator further includes a differential amplifier 216, which amplifies a difference between the node 214, and the reference voltage 182. The differential amplifier 216 also includes a capacitor 218 in parallel with a resistor 220 to provide feedback between the measured output voltage 130 and the node 214.

In various embodiments, the switches 210 and 212 are formed by complementary pairs of FETs configured, through appropriate transistor dimensioning, to minimize charge injection from the clock phase to the respective differentiator capacitor when the respective differentiator capacitor is being reset (e.g. shorted by the switch). In various embodiments, the first differentiator capacitor 204 has a same capacitance as the second differentiator capacitor 206, within reasonable manufacturing tolerances. In other embodiments the order of the two differentiator capacitors, (and similarly for the two integrator capacitors), is transposed. In other embodiments of the differentiator 128, the first clock phase 172 controls the second switch 212, and the second clock phase 174 controls the first switch 210. Similarly for other embodiments of the integrator 122, the first clock phase 172 controls the controls the second switch 192, and the second clock phase 174 controls the first switch 190.

Through the use of non-overlapping clock phases, only one capacitor integrates charge in the feedback loop of the integrator, while the other capacitor remains reset. During the reset of the charged capacitor, the integrated charge is equalized locally across the capacitor without requiring additional current to be drawn from the differential amplifier 180. In various embodiments, the local charge balancing occurs faster than the settling time of the differential amplifier 180. Consequently, large transients are avoided on the integrated voltage 126, which could otherwise cause the differentiator 128 to saturate, thereby producing a long recovery time during which the input current 124 is not observable and information may be lost. Furthermore, the integrator never enters unity gain feedback in contrast to embodiment 80 of FIG. 5. Consequently, the integrated voltage 126 does not experience an undesirable offset further promoting saturation of the differentiator 128. Other example embodiments of the self-resetting continuous-time architecture of FIG. 6 include more than two integrator capacitors and more than two differentiator capacitors, wherein all but one of the integrator capacitors are shorted at one time, and all but one of the differentiator capacitors are shorted at one time. In one example, a self-resetting continuous-time architecture includes four integrator capacitors, four differentiator capacitors and a multi-phase device, similar to the multi-phase device 170 of FIG. 7 to generate four non-overlapping clock phases. Each clock phase opens each one of the four integrator capacitors in succession, while resetting the remaining integrator capacitors. Each clock phase also opens each one of the four differentiator capacitors in succession, while resetting the remaining differentiator capacitors.

Figure 8:
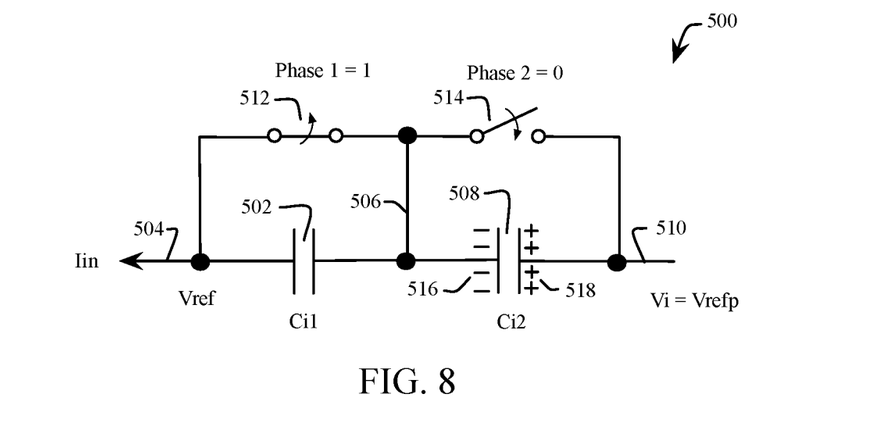
FIG. 8 is a schematic view of the resettable capacitors of FIG. 7 prior to an integrated voltage exceeding a voltage range.
Figure 9:
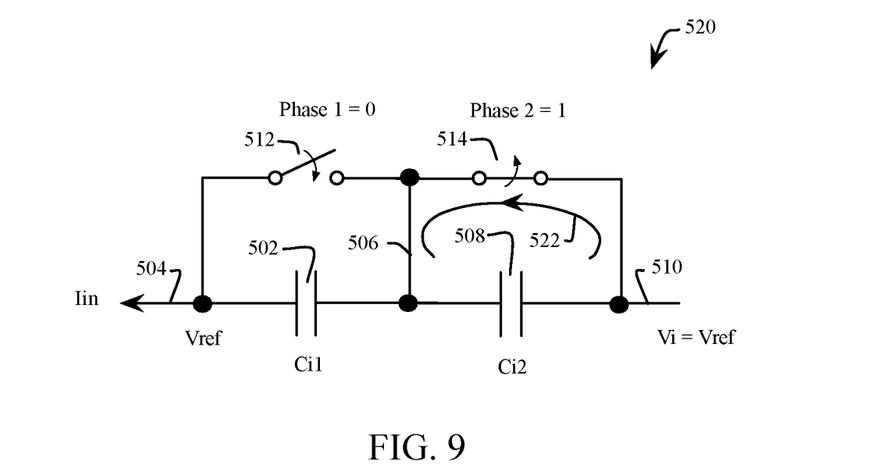
FIG. 9 is a schematic view of the resettable capacitors of FIG. 7 after the integrated voltage exceeds the voltage range.

FIG. 8 and FIG. 9 show further detail of the local charge balancing that occurs within the integrator 122 of FIG. 7. While the capacitors shown in FIG. 8 and FIG. 9 show the operation of the resettable capacitors 184 and 186 of the integrator 122, the same teachings and operation apply to the resettable capacitors 204 and 206 of the differentiator 128. With reference to FIG. 7 and FIG. 8, a first capacitor 502 is connected between an inverted input 504 (to the amplifier 180) and a node 506. A second capacitor is connected between the node 506 and the integrated voltage 510. A first switch 512 is connected between the parallel with the first capacitor 502. A second switch 514 is connected in parallel with the second capacitor 508.

While the integrator 122 is integrating an input current 124 at the inverted input 504, the first clock phase 172 (e.g. Phase 1) shorts the first capacitor 502 by the first switch 512, and the second clock phase 174 (e.g. Phase 2) opens the second switch 514. The amplifier 180 seeks to equalize the voltage at the inverted input 504 to match the reference voltage 182 (e.g. Vref) through negative feedback by charging the second capacitor 508. The integrated voltage output 510 of the amplifier 180 deposits a negative charge 516 on the plate of the second capacitor 508, thereby lowering the voltage at 504 to be equal to Vref. The integrated voltage output 510 of the amplifier 180 also deposits an equivalent positive charge 518 on the opposing plate of the second capacitor 508, thereby increasing the voltage of the integrated voltage output 510 towards the positive reference voltage 134. When the integrated voltage output 510 exceeds the positive reference voltage 134 and the hysteresis of the positive threshold comparator 136, the first switch 512 is opened, enabling further charging to occur on the first capacitor 502. In one embodiment, the second switch 514 is shorted after a short time to prevent direct conduction from the integrated voltage 510 to the inverted input 504 (e.g. unity gain feedback). In another embodiment, the first switch 512 closes at the same time that the second switch 514 opens, with a short, but undesirable, period of unity gain feedback. When the second switch 514 shorts the second capacitor 508, local charge balancing 522 occurs without drawing further charge from the output of the amplifier 180. Specifically, the negative charge 516 and the positive charge 518 combine to form a zero net charge across the second capacitor 508. A similar process occurs when the input current 124 at the inverted input 504 has a negative polarity and the integrated voltage 510 is discharged to level less than the negative reference voltage 154, in which case the second capacitor 508 will receive a positive charge 518 on the capacitor plate connected to the inverted input 504 and a negative charge 516 on the capacitor plate connected to the integrated voltage 510.

Figure 10:
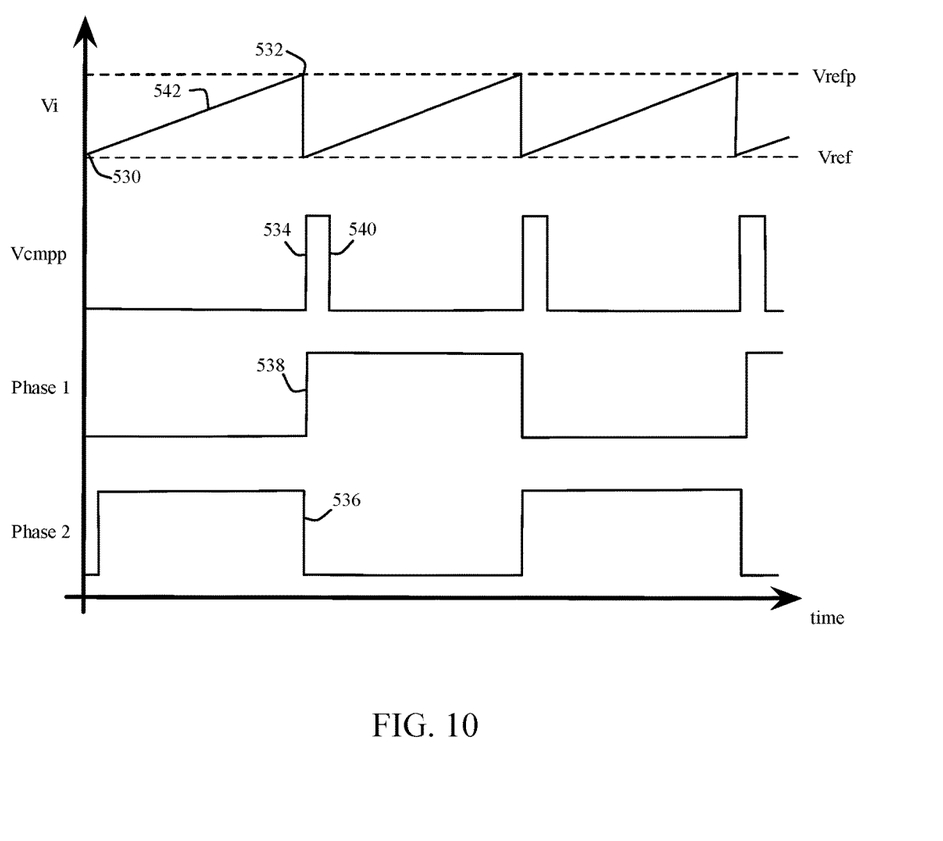
FIG. 10 is timing diagram of a method for self-resetting a continuous-time integrator-differentiator in accordance to an embodiment of the present disclosure.

Turning now to FIG. 10, and with reference to FIG. 7, the timing of the self-resetting continuous-time integrator-differentiator is explained. After opening the first integrator switch 190, (and closing the second integrator switch 192) the first integrator capacitor 184 is initially discharged with both capacitor plates of the first integrator capacitor 184 at the Vref 182 potential. Accordingly, the integrated voltage 126 will be equal to the reference voltage 182 (Vref) at a time 530. The first integrator capacitor 186 will charge to a voltage level equal to the positive reference voltage 134 plus the hysteresis of the positive voltage comparator 136 at a time 532. When the positive threshold comparator 136 switches at time 534, the positive comparator voltage 138 is asserted (e.g. transitions to a higher voltage), thus causing a transition in the multi-phase device 170. The multi-phase device 170 will first deassert the second clock phase 174 at time 536, thereby opening the second switch 192, and then assert the first clock phase 172 at time 538 to close the first switch 190. The accumulated charge on the first integrator capacitor 184 will be discharged through local charge balancing thus restoring the integrated voltage 126 to be equal to the reference voltage 182 and deasserting the positive comparator voltage at time 540. Once the second switch 192 has opened, the second integrator capacitor 186 will then begin charging.

A rate 542 at which the first integrator capacitor 184 is charged is given by the following formula, where "Foutp" is the positive frequency output 144, "Iin" is the input current 124, "Vrefp" is the positive reference voltage 134 (including comparator hysteresis), "Vref" is the reference voltage 182, and "Cil" is the integrator capacitor 184:

$$Foutp = Iin/[2*(Vrefp-Vref)*Cil]$$

The above equation can be similarly applied to charging the second integrator capacitor, which in various embodiments has the same capacitance as the first integrator capacitor. Similarly, a negative input current 124 will produce a frequency inversely proportional the difference between the negative voltage reference 154 and the reference voltage 182. In various embodiments the voltage differential produced at the integrated voltage 126 output is chosen to prevent the differentiator 128 from saturating.

Figure 11:
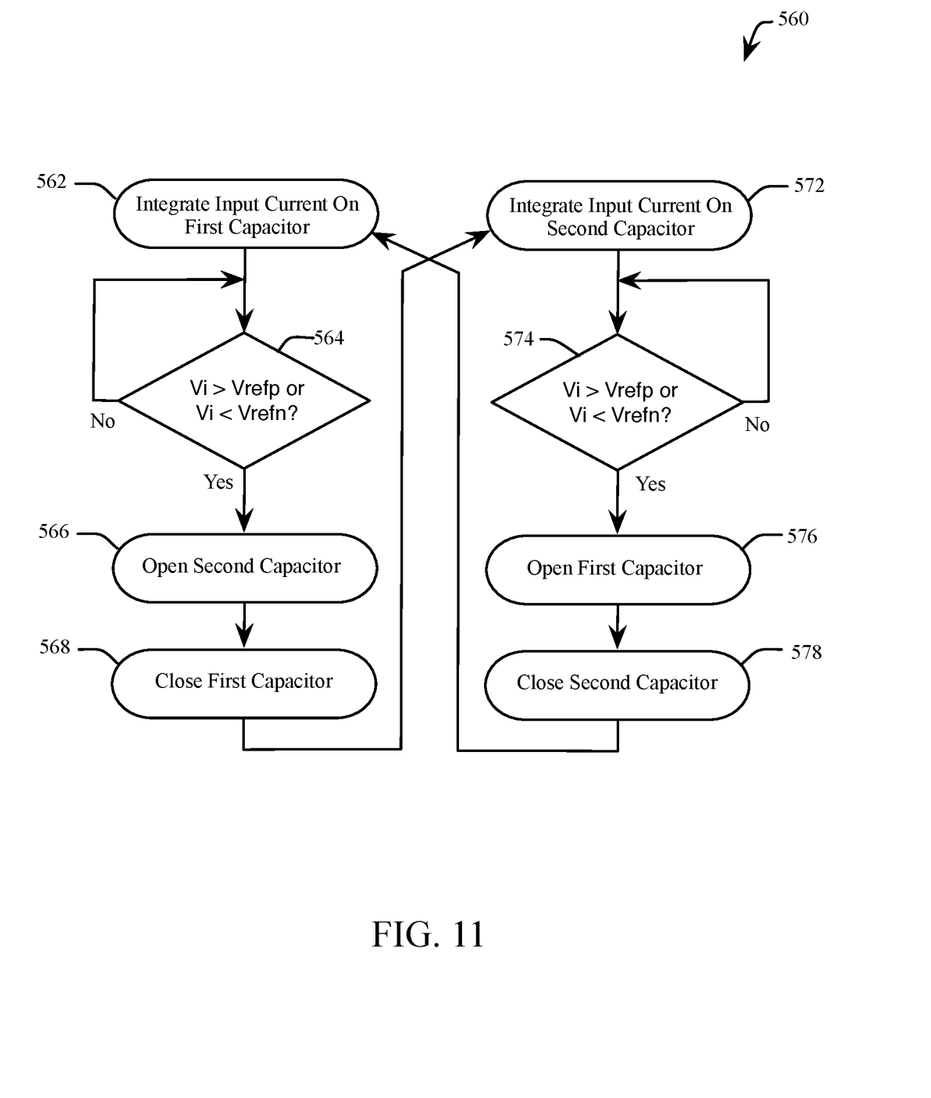
FIG. 11 is a flowchart representation of a method for self-resetting a continuous-time integrator-differentiator for high-speed diagnostics.

FIG. 11 is a flowchart representation 560 further describing the alternative charging of the two capacitors of the integrator 122 of FIG. 7. At 562, the input current 124 is integrated on the first integrator capacitor 184 (e.g. while the first switch 190 is open and the second switch 192 is closed or following 578). At 564 the integrated voltage 126 is compared with a positive reference voltage 134 and a negative voltage reference 154, in one embodiment. In other embodiments, the integrated voltage 126 is compared with either the positive reference voltage 134 or the negative voltage reference 154. When the integrated voltage 126 is greater than the positive reference voltage 134 or less than the negative reference voltage 154 (e.g. the integrated voltage 126 exceeds a voltage range), the second integrator capacitor 186 is opened at 566, and the first integrator capacitor 184 is closed at 568.

After the first integrator capacitor 184 is closed at 568, at 572, the input current 124 is integrated on the second integrator capacitor 186 (e.g. while the first switch 190 is closed and the second switch 192 is open). At 574 the integrated voltage 126 is compared with a positive reference voltage 134 and a negative voltage reference 154, in one embodiment. In other embodiments, the integrated voltage 126 is compared with either the positive reference voltage 134 or the negative voltage reference 154. When the integrated voltage 126 exceeds either the positive reference voltage 134 or the negative reference voltage 154, the first integrator capacitor 184 is opened at 576, the second integrator capacitor 186 is closed at 578 and the input current 124 is then integrated on the first integrator capacitor 184 at 562.

Various combinations of the aforementioned embodiments of self-resetting continuous-time integrator-differentiator topologies provide for concurrent voltage and frequency outputs. In some embodiments, the differentiator 128 is eliminated for a simpler implementation but with a reduction in measurement resolution. The voltage output 130 and the frequency output 144 (and 164) are each proportional to the input current 124 and together provide high resolution while maintaining high bandwidth without increasing the noise floor that typically accompanies topologies that support large input current magnitudes. The aforementioned embodiments also eliminate the need for external clocks, thus the bandwidth is not constrained by sample rate. Furthermore both the integrator 122 and the differentiator 128 are reset in a charge-conserving manner thus reducing voltage transients, amplifier saturation and extended recovery times. These non-exhaustive and non-limiting advantages of the aforementioned embodiments enable faster, cheaper and higher fidelity diagnostics applicable to numerous fields, including but not limited to DNA sequencing, and single-molecule protein detection.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

What is claimed is:

1. A method for high-speed molecular diagnostics comprising:
   integrating an input current to generate an integrated voltage proportional to a first integrated charge stored thereby on a first resettable capacitor of an integrator;
   switching between a first one and a second one of a plurality of clock phases in response to the integrated voltage exceeding a voltage range;
   shorting the first resettable capacitor with a first switch controlled by the first one of the plurality of clock phases to equalize the first integrated charge stored on the first resettable capacitor; and
   opening a second resettable capacitor with a second switch controlled by a second one of the plurality of clock phases, wherein the second resettable capacitor is connected in series with the first resettable capacitor in a negative feedback loop of the integrator.

2. The method of claim 1 further comprising differentiating the integrated voltage to generate an output voltage proportional to the input current.

3. The method of claim 2 further comprising:
   shorting a third resettable capacitor with a third switch controlled by the first one of the plurality of clock phases to equalize a differentiated charge stored on the third resettable capacitor by an differentiator, and
   opening a fourth resettable capacitor with a fourth switch controlled by the second one of the plurality of clock phases, wherein the fourth resettable capacitor is connected in series with the third resettable capacitor forming an input to the differentiator.

4. The method of claim 2 further comprising:
shorting a third resettable capacitor with a third switch controlled by the second one of the plurality of clock phases to equalize a differentiated charge stored on the third resettable capacitor by an differentiator, and
opening a fourth resettable capacitor with a fourth switch controlled by the first one of the plurality of clock phases, wherein the fourth resettable capacitor is connected in series with the third resettable capacitor forming an input to the differentiator.

5. The method of claim 1 further comprising generating an output frequency having a frequency proportional to the input current, by toggling a bistable device in response to the integrated voltage exceeding the voltage range.

6. The method of claim 1 wherein the integrated voltage exceeding the voltage range comprises one of the integrated voltage being greater than an upper threshold voltage and the integrated voltage being less than a lower threshold voltage.

7. The method of claim 1 further comprising integrating the input current on the second resettable capacitor to generate the integrated voltage proportional to a second integrated charge stored thereby, in response to opening the second resettable capacitor with the second switch.

8. The method of claim 7 wherein the first integrated charge is equal to the second integrated charge.

9. A device for high-speed molecular diagnostics comprising:
an integrator configured to generate an integrated voltage by integrating an input current received thereto, the integrator comprising a first resettable capacitor connected in series with a second resettable capacitor in a negative feedback loop of an amplifier,
a first comparator configured to switch a state of a first multiphase device in response to the integrated voltage of the integrator exceeding a first threshold voltage of the first comparator, wherein the first multiphase device provides a plurality of non-overlapping clock phases;
a first switch connected in parallel with the first resettable capacitor, the first switch controlled by a first one of the plurality of non-overlapping clock phases; and
a second switch connected in parallel with the second resettable capacitor, the second switch controlled by a second one of the plurality of non-overlapping clock phases.

10. The device of claim 9 further comprising:
a differentiator configured to generate an output voltage proportional to the input current comprising a third resettable capacitor and a fourth resettable capacitor connected in series between the integrated voltage and an inverting input of an amplifier,
the third resettable capacitor configured to be shorted when the fourth resettable capacitor is open, and
the fourth resettable capacitor configured to be shorted when the third resettable capacitor is open.

11. The device of claim 9 further comprising a bistable device configured to generate an output frequency having a frequency proportional to the input current in response to the integrated voltage exceeding the voltage range.

12. The device of claim 9 further comprising a second comparator having a second threshold voltage, the state of the first multiphase device switching in response to the voltage output of the integrator exceeding one of the first threshold voltage and the second threshold voltage.

13. The device of claim 12 wherein at least one of the first threshold voltage and the second threshold voltage includes a hysteresis value.

14. The device of claim 9 wherein the first resettable capacitor has a first capacitance equal to a second capacitance of the second resettable capacitor.

15. The device of claim 9 wherein at least one of the first switch and the second switch comprises a complementary pair of field effect transistors.

16. A system for high-speed molecular diagnostics comprising:
a self-resetting continuous-time integrator configured to integrate an input current on one of a plurality of integration capacitors to generate an integrated voltage;
a self-resetting continuous-time differentiator configured to differentiate the integrated voltage on one of a plurality of differentiating capacitors to generate an output voltage proportional to the input current; and
a fixed-threshold window comparator configured to reset the one of the plurality of integration capacitors, reset the one of the plurality of differentiating capacitors, open a second one of the plurality of integration capacitors and open a second one of the plurality of differentiating capacitors in response to the integrated voltage exceeding a voltage range.

17. The system of claim 16 further comprising a bistable device configured to generate an output frequency proportional to the input current by toggling in response to the integrated voltage exceeding the voltage range.

18. The system of claim 16 wherein the input current is an ionic current conducting through a nanopore.

19. The system of claim 16 wherein the input current is an electron tunneling current conducted through a molecule in a tunneling gap.

20. The system of claim 16 wherein the input current is used for one of DNA sequencing and biomolecule detection.

* * * * *